United States Patent

Webb

[11] Patent Number: 5,921,990
[45] Date of Patent: Jul. 13, 1999

[54] COLLAGEN FORCEPS

[75] Inventor: Nicholas J. Webb, Wrightwood, Calif.

[73] Assignee: Eagle Vision, Memphis, Tenn.

[21] Appl. No.: 08/907,199

[22] Filed: Aug. 6, 1997

[51] Int. Cl.[6] .................................................. A61B 17/24
[52] U.S. Cl. ....................... 606/110; 606/205; 606/206; 606/107
[58] Field of Search .................. 606/205, 206, 606/207, 210, 211, 107

[56] References Cited

U.S. PATENT DOCUMENTS

| | | | |
|---|---|---|---|
| 4,257,406 | 3/1981 | Schenk | 128/20 |
| 4,726,367 | 2/1988 | Shoemaker | 128/303 R |
| 5,015,252 | 5/1991 | Jones | 606/205 |
| 5,019,091 | 5/1991 | Porat et al. | 606/205 |
| 5,156,431 | 10/1992 | Lowe | 294/99.2 |
| 5,176,696 | 1/1993 | Saunders | 606/174 |
| 5,178,622 | 1/1993 | Lehner, II | 606/107 |
| 5,217,464 | 6/1993 | McDonald | 606/107 |
| 5,292,324 | 3/1994 | McDonald | 606/107 |
| 5,556,403 | 9/1996 | Michalos | 606/148 |
| 5,630,821 | 5/1997 | Klaas | 606/205 |
| 5,792,137 | 8/1998 | Carr et al. | 606/29 |

*Primary Examiner*—Gary Jackson
*Assistant Examiner*—Lien Ngo

*Attorney, Agent, or Firm*—David P. Gordon; David S. Jacobson; Thomas A. Gallagher

[57] ABSTRACT

A collagen forceps includes two elongate members coupled at a proximal live hinge. Each elongate member is provided with a knurled finger pad ergonomically contoured to stably receive a finger or thumb of a physician, and a manipulation tip having an interior collagen rod gripping surface. The gripping surfaces each include an angulated or curved surface provided with ridges and shaped to engage the collagen rod axially with the elongate members. Preferably each manipulation tip is also provided with a silicon boot. In addition, the instrument is also provided with a projection having a dilation/insertion tip. The collagen forceps of the invention enables a more controlled implantation of collagen rods through the punctal opening and into the naso-lacrimal duct. The contoured finger pads provide a physician with a more comfortable and more controllable instrument. The gripping surfaces of the manipulation tips, especially when provided with silicon boots, enable easy grasping of the collagen rods and stably engage the rods such that the collagen rod cannot rotate about or slide away from the gripping surfaces. As such, the collagen forceps permits relatively easy manipulation of the rods into the ducts. The dilation/insertion tip of the projection can be used to dilate the punctal opening to facilitate collagen rod insertion therein, and may also be used to push the collagen rod deep into the punctal opening.

22 Claims, 3 Drawing Sheets

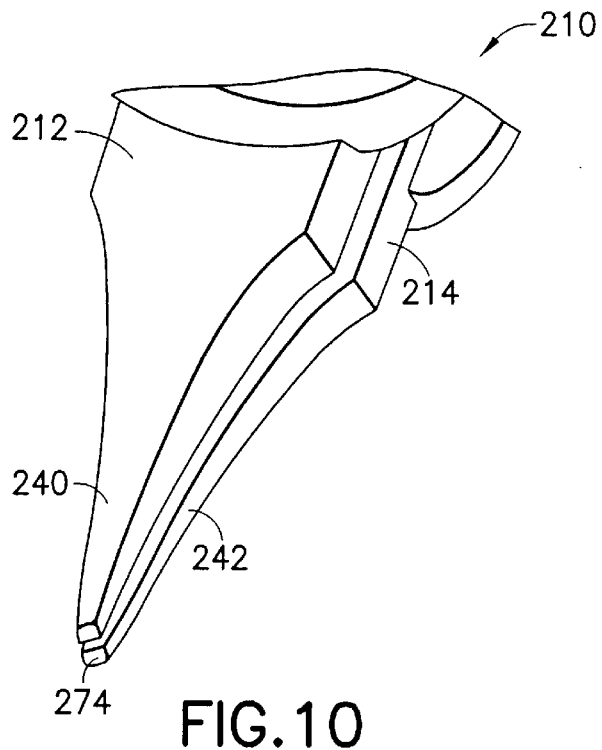
FIG. 10
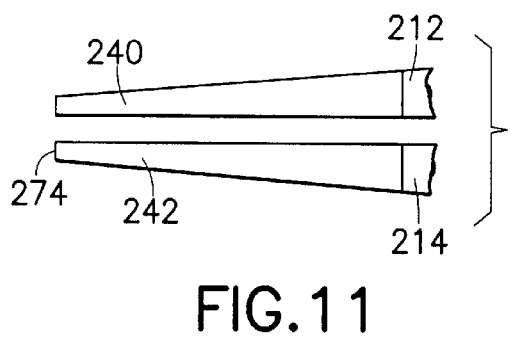
FIG. 11
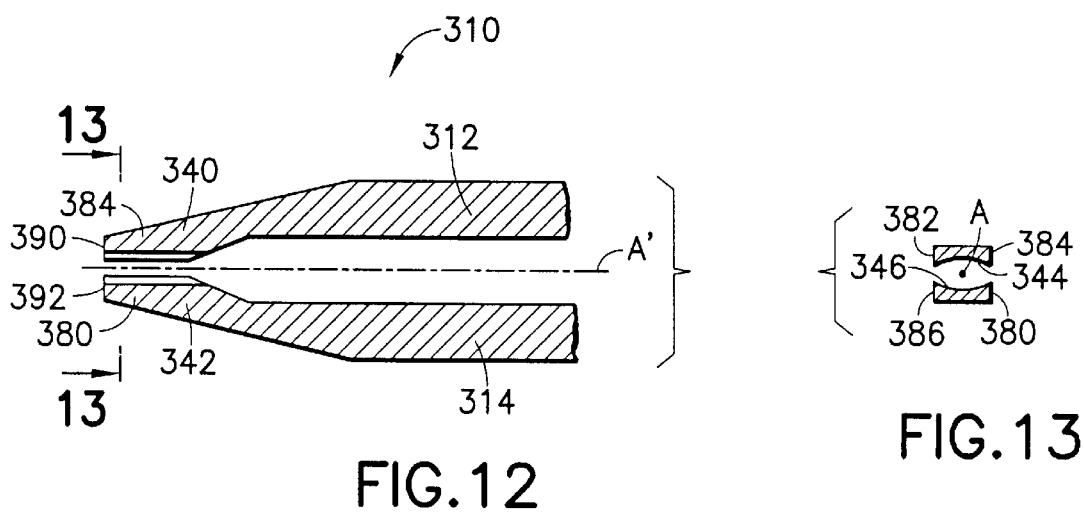
FIG. 12
FIG. 13

COLLAGEN FORCEPS

BACKGROUND OF THE INVENTION

1. Field of the Invention

This invention relates broadly to ophthalmological instruments. More particularly, this invention relates to instruments used to insert collagen rods into the punctal opening.

2. State of the Art

A variety of eye problems are related to an insufficient volume of tears on the surface of the eyes. The most common is keratoconjunctivitis sicca, also known as dry eyes. Contact lens problems are also often provoked by a lacks of tear volume. A common cause for the insufficient tear volume is the drainage of tear fluid through the punctal opening of the nasal lacrimal duct and into the nasal passage, thereby removing the fluid from where it is needed at the eye surface. Furthermore, drainage of tear fluid through the nasal lacrimal duct into the nasal passage is believed to be the cause or associated with several additional problems such as post nasal drip, sinusitis, allergies, headaches, and snoring.

A number of methods for closing the punctal opening have been used to prevent drainage of tears through the nasal lacrimal duct, including suturing, laser sealing, and plugging. However, before any of the above methods are used on a patient, small collagen rods are often implanted into the punctal openings in the eyes of the patient to occlude the nasal lacrimal ducts. The physician treating the patient can then better diagnose the patient. The collagen rod implants slowly dissolve in about a week, giving the physician ample time to verify the potential clinical benefits of more permanent occlusion for a particular patient, and also to evaluate receptivity of the patient to duct occlusion.

The collagen rods intended for occluding the nasal lacrimal ducts are extremely small (approximately 2 mm in length and having a diameter of approximately 0.2 mm). Because of the small size of the collagen rods, a tool is required to insert the rods into the punctal opening. Referring now to prior art FIG. 1, the tool of the prior art used to insert collagen rode is typically a straight collagen forceps 10, the shape and size of a conventional tweezers. The collagen forceps has two arms 12, 14 resiliently hinged at a proximal portion 16 and terminating distally in two elongate tips 18, 20. Each tip has an inner flat surface 22, 24 which grips the collagen rod. The arms 12, 14, which are held by the physician, are relatively narrow and do not provide comfortable and stable finger and thumb grips. Comfortable and stable finger and thumb grips are desirable when working with very small implants close to the eye, as fine manipulation of the elongate tips is required to implant the rods into the punctal openings of the eyes. Additionally, the inner gripping surfaces 22, 24 are inadequate for gripping cylindrical collagen rods as the rods tend to slip against and rotate on the flat surface. Furthermore, prior art forceps instruments are unable to provide pre-insertion dilation of the punctal opening, nor do they have the ability to push the collagen rod into the punctal opening such that the collagen rod is pushed below the punctal opening. A second instrument is required for those purposes.

SUMMARY OF THE INVENTION

It is therefore an object of the invention to provide a collagen forceps designed to easily insert a collagen rod into the punctal opening.

It is another object of the invention to provide a collagen forceps which is comfortable to hold and which thereby permits easy and fine manipulation of the collagen rods.

It is also an object of the invention to provide a collagen forceps which can securely grip the collagen rod.

It is an additional object of the invention to provide a collagen forceps having the ability to predilate the punctal opening.

It is also an object of the invention to provide a collagen forceps having which can be used to fully insert collagen rods beneath the punctal opening.

In accord with these objects which will be discussed in detail below, a collagen forceps is provided. According to the preferred embodiment of the invention, the collagen forceps generally includes two elongate members coupled at a proximal live hinge. The elongate members are each provided with a knurled finger pad ergonomically contoured to stably receive a finger or thumb of a physician, and a manipulation tip having an interior collagen rod gripping surface. The gripping surface of each elongate member includes an angulated or curved concave surface shaped to engage the collagen rod axially and is preferably provided with rod engagement ridges. Preferably each manipulation tip is also provided with a silicon boot. In addition, the proximal end of the instrument is provided with a projection having a dilation/insertion tip.

The collagen forceps of the invention enables a controlled implantation of collagen rods through the punctal opening and into the naso-lacrimal duct. The contoured finger pads provide a physician with a comfortable and controllable instrument. The gripping surfaces of the manipulation tips, especially when provided with silicon boots, permit easy grasping of the collagen rods and stably engage the rods such that the collagen rod cannot rotate about or slide away from the gripping surfaces. As such, the collagen forceps permits relatively easy manipulation of the rods into the ducts. In addition, the dilation/insertion tip of the projection can be used to dilate the punctal opening prior to collagen rod insertion therein, and may also be used after the insertion of the collagen rod to push the collagen rod deeper into the punctal opening.

According to second and third embodiments, dilation/insertion means are provided at the distal end of the instrument on one or both of the elongate members.

Additional objects and advantages of the invention will become apparent to those skilled in the art upon reference to the detailed description taken in conjunction with the provided figures.

BRIEF DESCRIPTION OF THE DRAWINGS

FIG. 10 is an enlarged broken perspective view of a third embodiment of a collagen forceps according to the invention;

FIG. 11 is enlarged broken side elevation view of the collagen forceps of FIG. 10;

FIG. 12 is an enlarged broken side elevation view of a fourth embodiment of a collagen forceps according to the invention; and FIG. 13 is a cross-section through line 13—13 in FIG. 12.

DETAILED DESCRIPTION OF THE PREFERRED EMBODIMENTS

Figure 1:
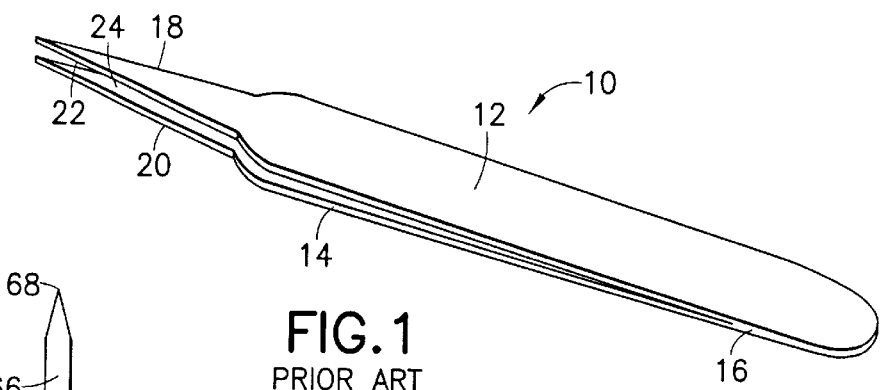
FIG. 1 is a prior art collagen forceps.
Figure 2:
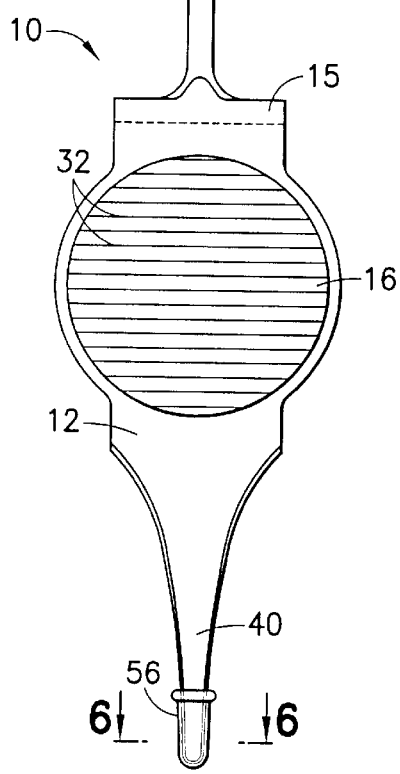
FIG. 2 is top view of the collagen forceps of the invention.
Figure 4:
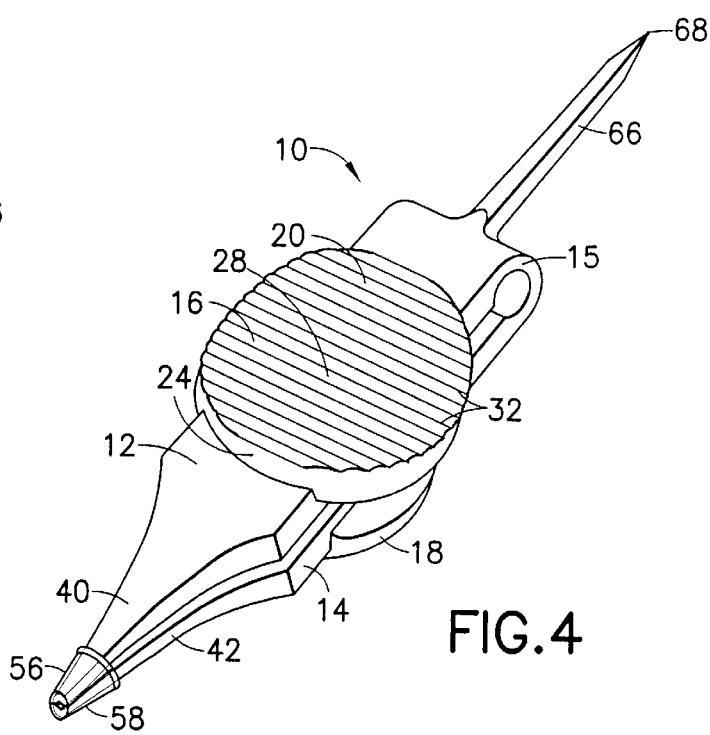
FIG. 4 is a perspective view of the collagen forceps shown in FIG. 2.
Figure 3:
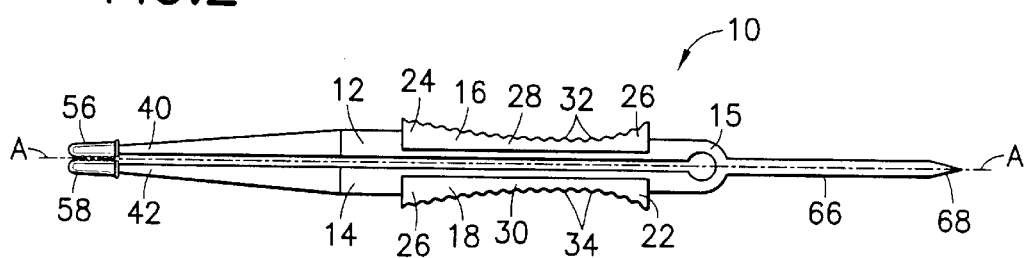
FIG. 3 is a side elevation view of the collagen forceps shown in FIG. 2.
Figure 5:
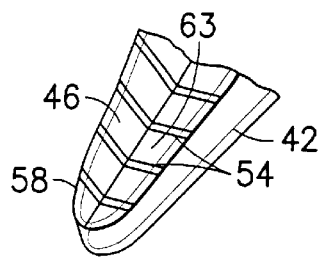
FIG. 5 is an enlarged broken perspective view of a distal tip of the collagen forceps shown in FIG. 4.
Figure 6:
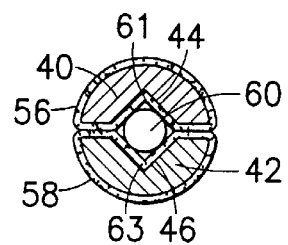
FIG. 6 is an enlarged side elevation of the boot of the collagen forceps of the invention.

Turning now to FIGS. 2 through 4, a collagen forceps 10 according to a first and preferred embodiment of the invention is shown. The collagen forceps 10 includes first and second elongate members 12, 14 coupled at a live hinge 15. The elongate members 12, 14 are preferably substantially parallel, and provided with a small separation from each other along their length. Each elongate member 12, 14 is provided with a finger pad 16, 18 which is preferably round or oval in shape. The finger pads 16, 18 are preferably wider than the width of the elongate members on either side of the finger pads. The first finger pad 16 is preferably ergonomically concavely contoured to comfortably receive one or more fingers of a physician, while the second finger pad 18 is preferably contoured to receive a thumb of the physician. A preferred contour of the first and second finger pads provides raised rear portions 20, 22 and front portions 24, 26 and relatively depressed central portions 28, 30. In addition, the finger pads 16, 18 are preferably provided with traction ridges 32, 34 (knurls) which are engaged by the finger(s) and thumb, and to prevent the finger(s) and thumb from slipping off the finger pads. The traction ridges are oriented substantially perpendicular to the longitudinal axis A of the forceps.

Figure 7:
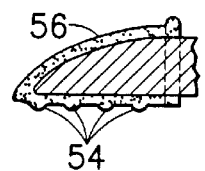
FIG. 7 is an enlarged cross-section across line 6—6 in FIG. 1, with the collagen forceps holding a collagen rod.

Referring now to FIGS. 2 through 6, each elongate member 12, 14 is also provided with a manipulation tip 40, 42 having an interior collagen rod gripping surface 44, 46. The gripping surfaces 44, 46 are preferably angulated or curved concave surfaces shaped to engage a collagen rod 60 axially within a groove 61, 63 formed by the surfaces (FIG. 6); i.e., the gripping surfaces engage the collagen rod at more than two lines of contact. Preferably each manipulation tip 40, 42 is also provided with a thin, flexible, silicon boot 56, 58 (FIG. 7) preferably provided with engagement ridges 54 which securely grip and hold the collagen rod. The boots 56, 58 are shaped to fit snugly over, and preferably contour to, the manipulation tips 40, 42 (FIGS. 2–4 and 6), and provide a high friction surface for easily gripping collagen rods. The silicon boots are preferably made from a 60 Durometer silicon.

Turning back to FIGS. 2 through 4, a projection 66 is provided adjacent the hinge 15 and is preferably directed in a direction opposite the elongate members 12, 14. The projection 66 includes a preferably tapered dilation/insertion tip 68.

In practice, the physician, preferably first inserts the dilation/insertion tip 68 of the projection 66 through the punctal opening to dilate the punctal opening. The physician then turns the instrument such that the tips 40, 42 are distally directed, and places one or two fingers on one finger pad 16, and a thumb on the other finger pad 18. When pressure by the physician's finger(s) and thumb on the finger pads is not substantial enough to move the manipulation tips 40, 42 toward each other, a space is provided between the tips for picking up a collagen rod. With light pressure on the finger pads, the physician is able to move the tips toward each other to securely grab a collagen rod from a working surface. As stated above, the boots 56, 58, if provided, assist in picking up and gripping a collagen rod. In addition, the contoured finger pads 16, 18 and traction ridges 32, 34 provide comfort to the physician and enable subtle control of the collagen forceps.

With a collagen rod being axially held by the gripping surfaces 44, 46, i.e., with the gripping surfaces gripping the collagen rod around its circumference, the physician manipulates the collagen rod into the dilated punctal opening. After pushing the collagen rod as deep as possible via manipulation of the tips 40, 42, the physician releases pressure on the finger pads 16, 18 to permit the tips to move apart and release the collagen rod from the gripping surfaces. If desired, the physician then turns the collagen forceps 10 around, and using the dilation/insertion tip 68 of the projection 66 further pushes the collagen rod into and below the punctal opening.

The collagen forceps is preferably molded from an acrylic plastic, providing an inexpensive and disposable instrument. The instrument may also be made from stainless steel, other metals, or other suitable medical grade materials.

By way of example, and with the understanding that other dimensions may also be used, dimensions for the collagen forceps of the first embodiment are hereby provided. The collagen forceps 10, from the manipulation tips 40, 42 to the dilation/insertion tip 68, has a length of approximately three inches. The finger pads 16, 18 each have a diameter of approximately three-quarter inches. The width of the elongate members 12, 14 on either side of the finger pads is approximately three-eighths inches. The projection 66 is approximately three-quarter inches in length and approximately 0.060 inches in diameter until it tapers to the dilation/insertion tip. The manipulation tips 40, 42 are approximately one inch in length, and have a gripping surface 44, 46 shaped to accommodate collagen rods having a diameter of approximately 0.2 mm to 0.6 mm.

Figure 8:
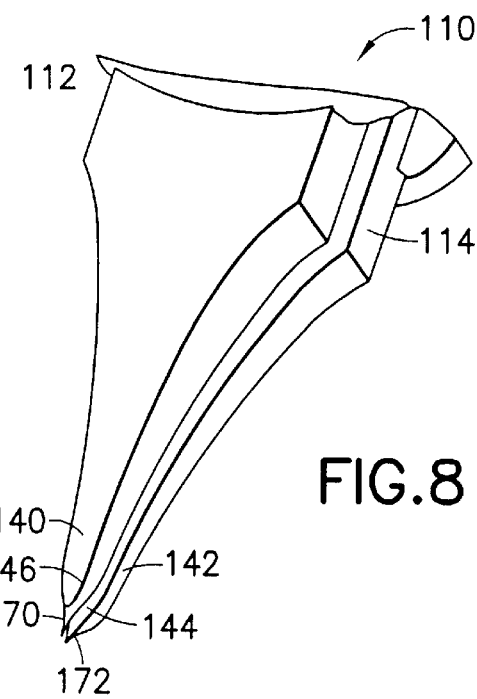
FIG. 8 is an enlarged broken perspective view of a second embodiment of a collagen forceps according to the invention.
Figure 9A:
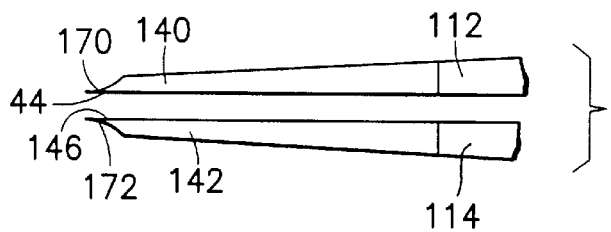
FIGS. 9A and 9B are enlarged broken side elevation views illustrating the collagen forceps of FIG. 8 in open and closed positions, respectively.
Figure 9B:
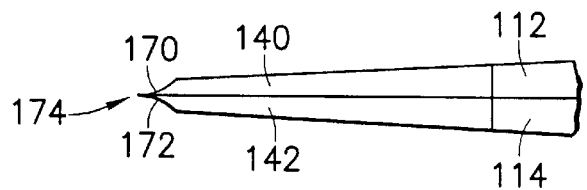

Turning now to FIG. 8, a second embodiment of a collagen forceps 110, substantially similar to the first embodiment (with like parts having numbers incremented by 100), is shown. Each elongate member 112, 114 is provided with a manipulation tip 140, 142 having an interior collagen rod gripping surface 144, 146. Each manipulation tip 140, 142 tapers toward the medial side of the respective tip (FIG. 9A), such that when the two tips 140, 142 are brought together in a closed position (FIG. 9B), a pointed dilator/inserter 174 is formed. The dilator/inserter 174 may be used in the same capacity as the dilation/insertion tip of the first embodiment.

Turning now to FIGS. 10 and 11, a third embodiment of a collagen forceps 210, substantially similar to the first embodiment (with like parts having numbers incremented by 200), is shown. Each elongate member 212, 214 is provided with a manipulation tip 240, 242. At least one manipulation tip 242 is provided with a dilator/insertion protuberance 274 extending distally from the manipulation tip. The dilator/inserter 274 may be used in the same capacity as the dilation/insertion tip of the first embodiment.

Turning now to FIGS. 12 and 13, a fourth embodiment of a collagen forceps 310, substantially similar to the first embodiment (with like parts having numbers incremented by 300), is shown. Each elongate member 312, 314 is provided with a manipulation tip 340, 342 having a curved interior collagen rod gripping surface 344, 346 which extends at lateral portions 380, 382, 384, 386 toward the longitudinal axis A' of the forceps. The manipulation tips at their most distal portions 390, 392 are sized, e.g, 0.06 inches across each manipulation tip and 0.01 inches down through the center of each manipulation tip, such that when they are brought together in a closed position, a dilator/inserter is formed.

There have been described and illustrated herein several embodiments of a collagen forceps. While particular embodiments of the invention have been described, it is not intended that the invention be limited thereto, as it is intended that the invention be as broad in scope as the art will allow and that the specification be read likewise. Thus, while particular contours for a finger pad have been disclosed, it will be appreciated that other contours can be used as well. Furthermore while ridges or knurls have been disclosed on the finger pads, it will be understood other traction means, e.g., grooves, can be used as well. Moreover, while the traction ridges or knurls have been described as being oriented perpendicular to the longitudinal axis of the forceps, it will be appreciated that the knurls on one or both of the finger pads may be at an angle other than perpendicular to the axis. Also, while a live hinge has been disclosed for coupling the elongate members, another coupling means may be used. In addition, while 60 Durometer silicon boots have been disclosed as being preferably provided to the manipulation tips, it will be appreciated that the boots are not required, and further that the boots, if provided, may be made of another silicon, e.g., 90 Durometer post cured silicon, or another material which provides friction between the manipulation tips and a collagen rod. Moreover, where the silicon boots are not provided, ridges may be provided directly to the gripping surfaces of the manipulation tips. Also, while a tapered dilation/insertion tip is disclosed, it will be appreciated that an insertion tip which is uniform in width over its length can be used to push the collagen rod below the punctal opening. In addition, while a proximal dilator/insertion tip is not required in the second and third embodiments, as the tips or a protuberance can be used to dilate the punctal opening and push the collagen rods, it will nonetheless be appreciated that a proximal dilation/insertion tip may additionally be provided. Moreover, while the dilation/insertion tip has been shown to extend substantially parallel to the longitudinal axis of the collagen forceps, it will be appreciated that the dilation/insertion tip may extend orthogonally to, or at another angle relative to, the elongate members, and may be straight, angled or curved. Furthermore, while the collagen forceps has been shown to be a straight instrument, the instrument may be angled such that the manipulation tips are non-axial with the finger pads. Moreover, while certain dimensions have been provided, it will be appreciated that other dimension could be used as well. It will therefore be appreciated by those skilled in the art that yet other modifications could be made to the provided invention without deviating from its spirit and scope as so claimed.

What is claimed is:

1. A collagen forceps for use by a practitioner to insert a collagen rod into a punctal opening of an eye, comprising:
    a) a first elongate member having a first end provided with a collagen rod gripping means, and a second end;
    b) a second elongate member having a first end provided with a collagen rod gripping means, and a second end;
    c) means for dilating the punctal opening of the eye, said means for dilating comprising projection directed substantially opposite said first end of said first elongate member, said projection coupled to at least one of said first and second elongate members; and
    d) coupling means hingeably coupling said second end of said first elongate member to said second end of said second elongate members.

2. A collagen forceps according to claim 1, wherein:
said means for at least one of dilating and pushing is a protuberance extending from said first end of said first elongate member.

3. A collagen forceps according to claim 1, wherein:
said projection is tapered.

4. A collagen forceps according to claim 1, wherein:
said collagen forceps has a longitudinal axis, and said collagen rod gripping means grip the collagen rod circumferentially when the collagen rod is substantially parallel to said longitudinal axis of said collagen forceps.

5. A collagen forceps according to claim 1, wherein:
said first elongate member includes a first finger engagement means contoured to stably receive one of a finger and thumb of said practitioner, and said second elongate member includes a second finger engagement means contoured to stably receive the other of a finger and thumb of said practitioner wherein the practitioner, by placement of his or her finger and thumb on the respective first and second finger engagement means and by movement of his or her finger and thumb toward each other, is able to move said gripping means of said first elongate member toward said gripping means of said second elongate member and releasably securably grip the collagen rod.

6. A collagen forceps according to claim 1, further comprising:
    d) a flexible boot provided over said first end of at least one of said first and second elongate members.

7. A collagen forceps according to claim 6, wherein:
said flexible boot is made of silicon and is provided with a plurality of ridges on a portion of said flexible boot which is used to grasp the collagen rod.

8. A collagen forceps having a longitudinal axis, said collagen forceps for use by a practitioner to insert a collagen rod having a longitudinal axis into a punctal opening of an eye, comprising:
    a) a first elongate member having a first end, a first collagen rod gripping means provided at said first end, and a first finger engagement means;
    b) a second elongate member having a first end, a second collagen rod gripping means provided at said first end, and a second finger engagement means; and
    c) coupling means for hingeably coupling said first and second elongate members,
    said first and second collagen rod gripping means for gripping the collagen rod along more than two longitudinal lines parallel to the longitudinal axis of the collagen rod when the collagen rod is substantially parallel to said longitudinal axis of said collagen forceps, and
    said finger engagement means of said first elongate member for receiving one of a finger or thumb of the practitioner, and said finger engagement means of said second elongate member for receiving the other of a finger or thumb of the practitioner,
    wherein the practitioner, by placement of his or her finger and thumb on said finger engagement means and by movement of his or her finger and thumb toward each other, is able to move said gripping means of said first elongate member toward said gripping means of said second elongate member and releasably securably grip the collagen rod.

9. A collagen forceps according to claim 8, wherein:

each of said first and second gripping means is a channel oriented substantially parallel to said longitudinal axis of said collagen forceps.

10. A collagen forceps according to claim 9, wherein:

said channel of one of said first and second gripping means includes at least one raised ridge oriented substantially perpendicular to said channel.

11. A collagen forceps according to claim 8, further comprising:

d) a flexible boot provided over said first end of at least one of said first and second elongate members.

12. A collagen forceps according to claim 11, wherein:

said flexible boot is made of silicon and is provided with a plurality of ridges on a portion of said flexible boot which is used to grasp the collagen rod.

13. A collagen forceps according to claim 8, wherein:

said first and second finger engagement means of each of said first and second elongate members is contoured to stably receive at least one of a finger and thumb of said practitioner.

14. A collagen forceps according to claim 8, further comprising:

d) means for at least one of dilating the punctal opening of the eye, and pushing the collagen rod below the punctal opening of the eye,
    said means for at least one of dilating and pushing being coupled to at least one of said first and second elongate members.

15. A collagen forceps according to claim 14, wherein:

said means for at least one of dilating and pushing is a projection extending from said coupling means.

16. A collagen forceps according to claim 8, wherein:

said first ends of said first and second elongate members are tapered toward said longitudinal axis of said collagen forceps, such that when said first and second gripping means of said first and second elongate members are moved toward each other, said tapered first ends form a means for at least one of dilating the punctal opening the punctal and pushing the collagen rod below the punctal opening of the eye.

17. A collagen forceps for use by a practitioner to insert a collagen rod into a punctal opening of an eye, comprising:

a) a first elongate member having a first end, a second end, and a first contoured finger pad;

b) a second elongate member having a first end, a second end, and a second contoured finger pad;

c) a live hinge coupling said second end of said first elongate member to said second end of said second elongate member,
    wherein said first and second elongate members and said live hinge are made from a unitary piece of material, and
    wherein said first and second contoured finger pads are concavely contoured to stably receive one of finger and thumb of the practitioner,
    such that when the practitioner places his or her finger and thumb on said first and second finger engagement means and moves his or her finger and thumb toward each other, the practitioner is able to move said first end of said first elongate member toward said first end of said second elongate member to releasably securely grip the collagen rod.

18. A collagen forceps according to claim 17, wherein:

said collagen forceps includes a longitudinal axis and said first ends of said first and second elongate members are tapered toward said longitudinal axis of said collagen forceps, such that when said first ends of said first elongate member and said first end of said second elongate member are moved toward each other, said tapered first ends form a means for at least one of dilating the punctal opening of the eye and pushing the collagen rod below the punctal opening of the eye.

19. A collagen forceps according to claim 17, further comprising:

d) means for at least one of dilating the punctal opening of the eye and pushing the collagen rod below the punctal opening of the eye,
    said means for at least one of dilating and pushing formed at said first end of at least one of said first and second elongate members.

20. A collagen forceps according to claim 17, further comprising:

d) a flexible boot provided over said first end of at least one of said first and second elongate members.

21. A collagen forceps according to claim 20, wherein:

said flexible boot is made of silicon and is provided with a plurality of ridges on a portion of said flexible boot which is used to grasp the collagen rod.

22. A collagen forceps according to claim 17, wherein:

said finger pads are provided with ridges engageable by the finger and thumb of the practitioner.

* * * * *